United States Patent [19]
Kenna

[11] Patent Number: 5,035,700
[45] Date of Patent: Jul. 30, 1991

[54] PROSTHETIC KNEE JOINT WITH IMPROVED PATELLAR COMPONENT TRACKING

[75] Inventor: Robert V. Kenna, Hobe Sound, Fla.

[73] Assignee: Pfizer Hospital Products Group, Inc., New York, N.Y.

[21] Appl. No.: 549,517

[22] Filed: Jul. 6, 1990

Related U.S. Application Data

[62] Division of Ser. No. 151,747, Feb. 3, 1988, Pat. No. 4,944,756.

[51] Int. Cl.⁵ ............................ A61F 2/32; A61F 5/00
[52] U.S. Cl. ......................................... 606/88; 606/87
[58] Field of Search ...................... 606/87, 88; 623/20, 623/66

[56] References Cited

U.S. PATENT DOCUMENTS 4,335,715  6/1982  Kirkley .................................. 606/87
4,739,751  4/1988  Sapega et al. ...................... 606/88 X

FOREIGN PATENT DOCUMENTS 2159680A 12/1985  United Kingdom .................. 606/87

*Primary Examiner*—Alan W. Cannon
*Attorney, Agent, or Firm*—Peter C. Richardson; Lawrence C. Akers; Elizabeth O. Slade

[57] ABSTRACT

A three-component knee joint prosthesis is disclosed including femoral, tibial and patellar components. During flexion of the prosthetic knee, the patellar component, which has a convex bearing surface, cooperates with and is guided by a patellar track defined by the anterior plate portion, lateral condylar bearing portion and medial condylar bearing portion of the femoral component and a web portion joining the two femoral condylar bearing portions. The inner regions of the two femoral condylar bearing portions are steeply sloped towards the web portion to permit the patellar component to "ride deeply" upon the femoral component at high degrees of flexion, thereby reducing quadriceps tension and expanding the permissible range of motion in flexion.

1 Claim, 5 Drawing Sheets

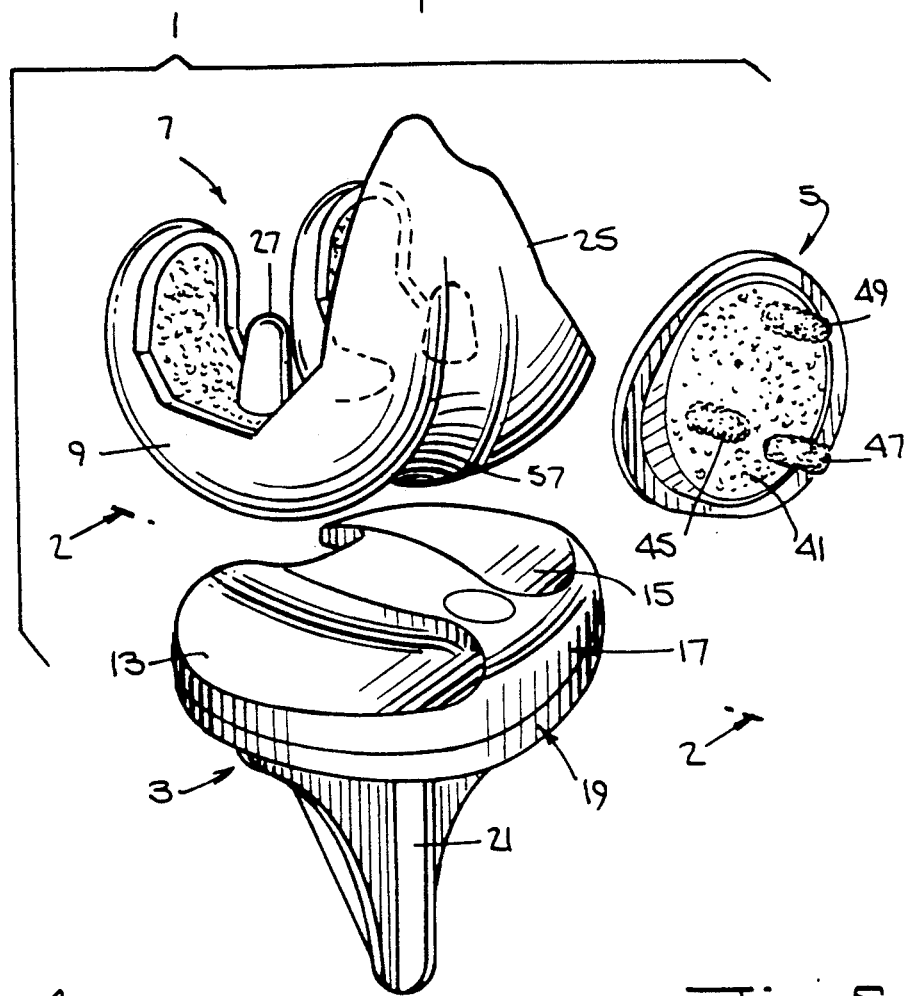
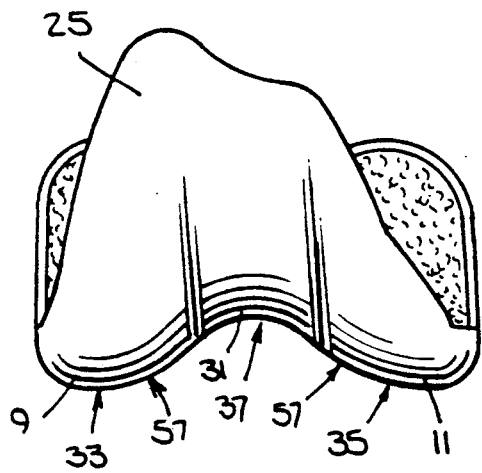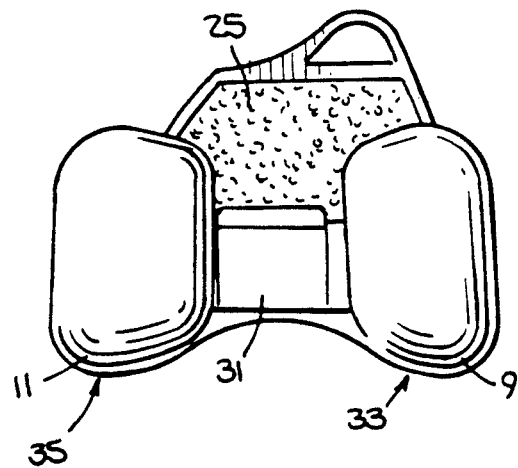

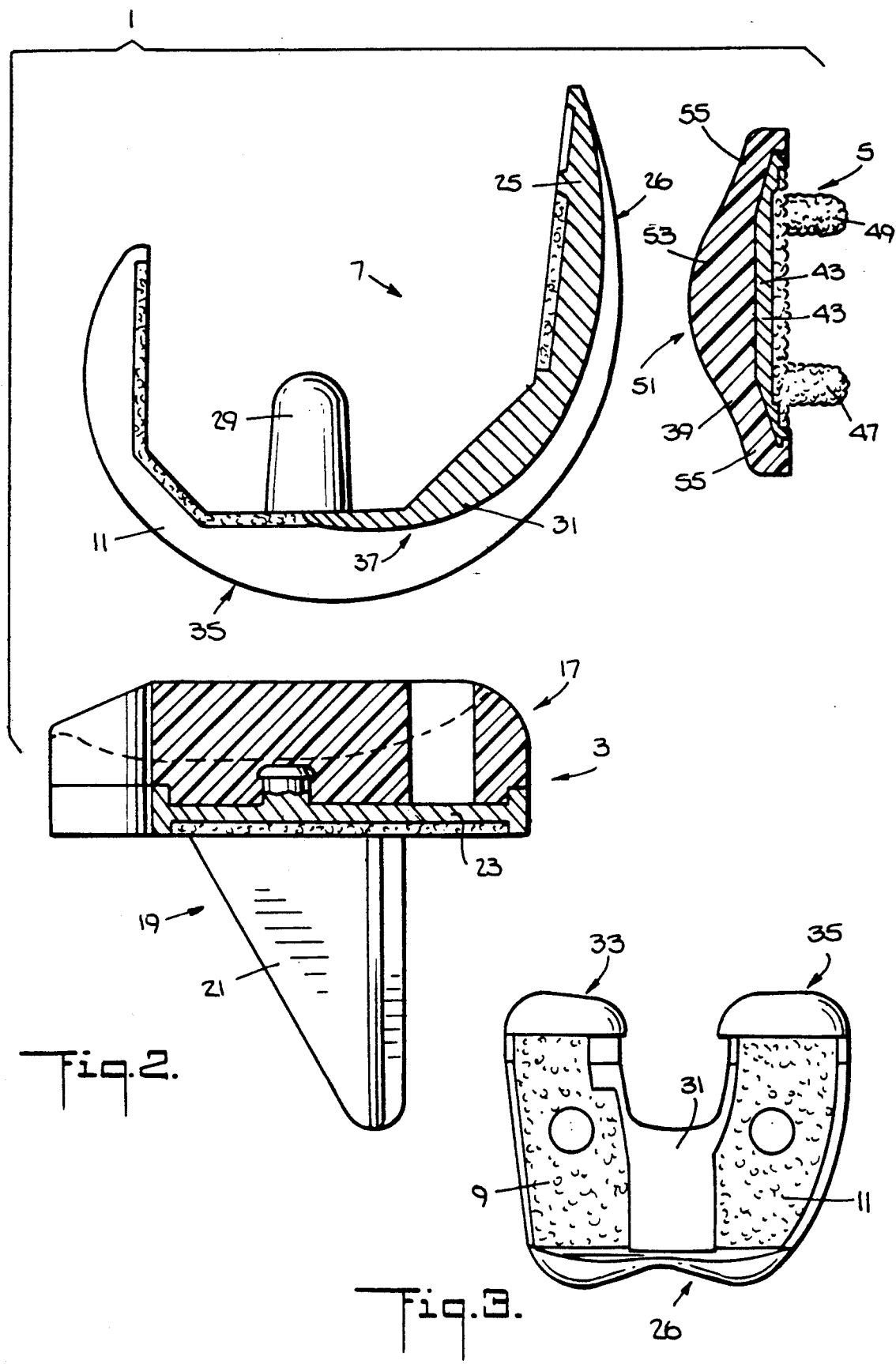

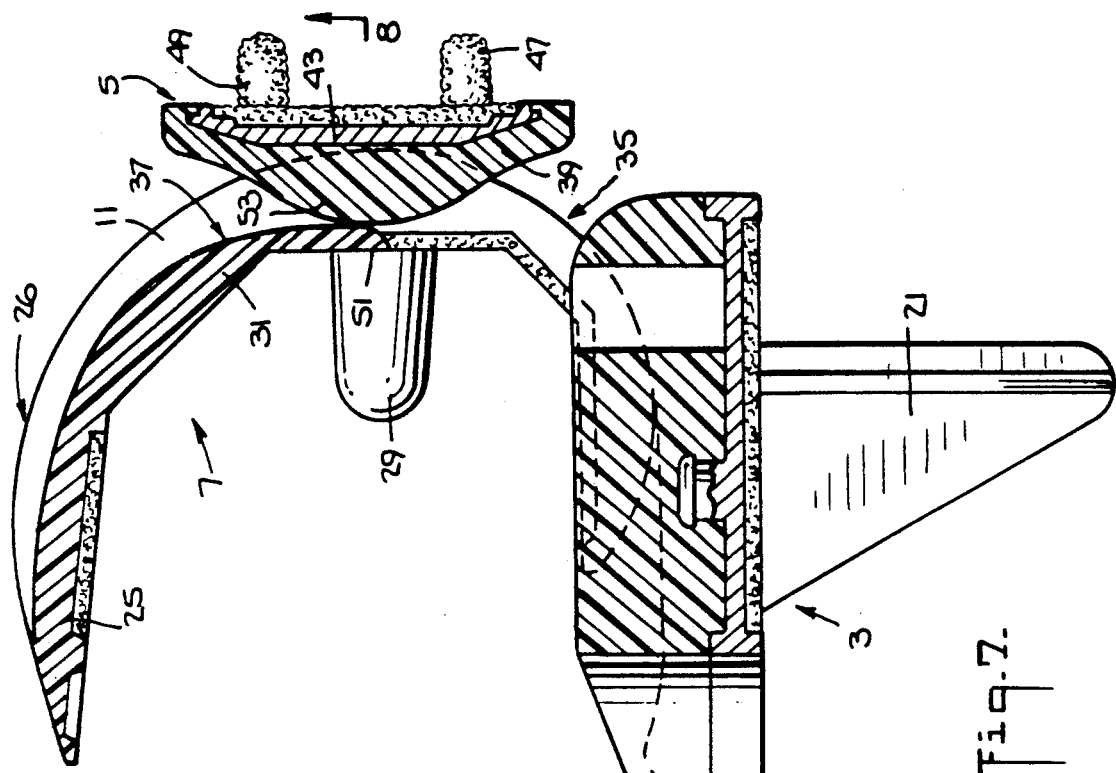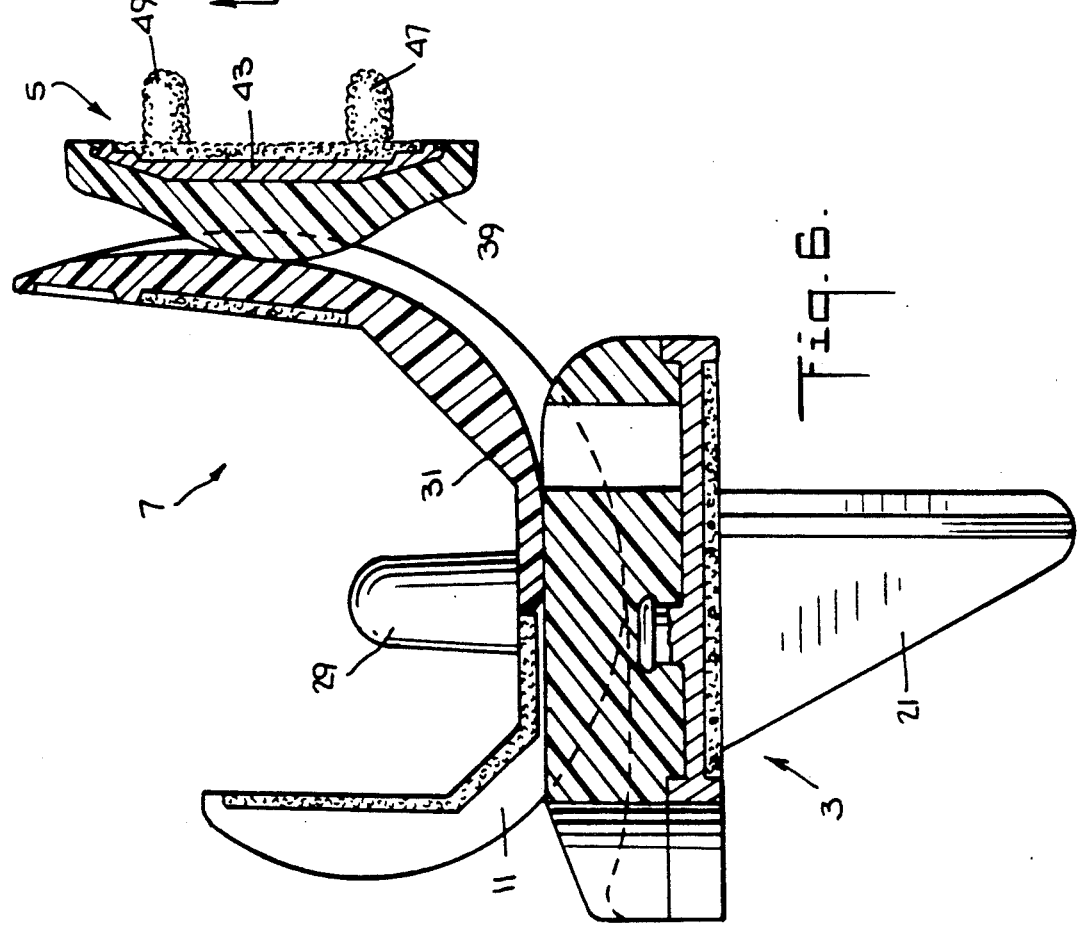

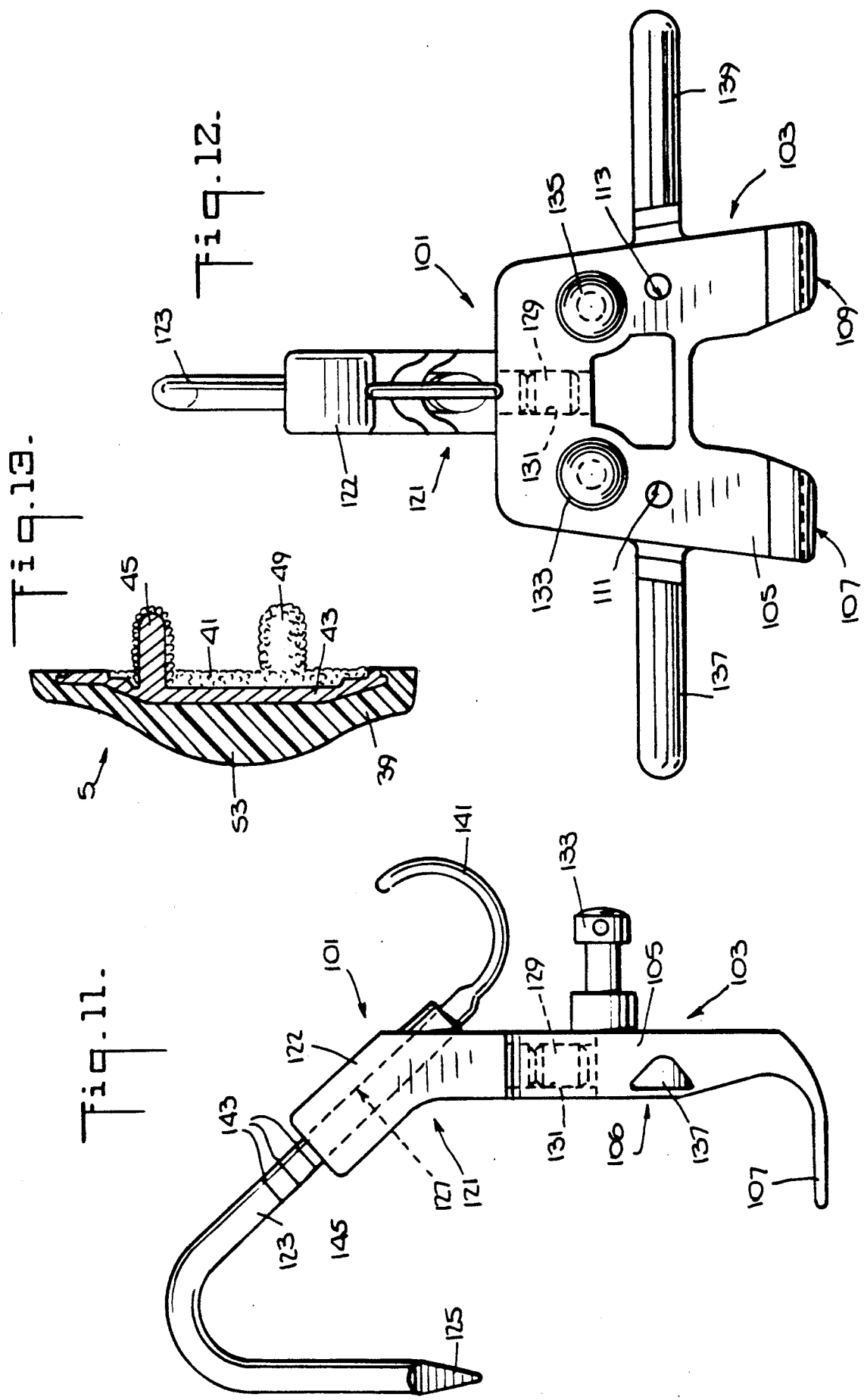

PROSTHETIC KNEE JOINT WITH IMPROVED PATELLAR COMPONENT TRACKING

This is a division, of application Ser. No. 07/151,747, filed on Feb. 3, 1988, now U.S. Pat. No. 4,944,756.

BACKGROUND OF THE INVENTION

Total knee arthroplasty, in which the natural femoral and tibial condylar bearing surfaces are replaced with prosthetic femoral and tibial components, has been practiced for many years with a high rate of success. One total knee prosthetic system that has been used with excellent results is the P.C.A. ® Total Knee System sold by the Howmedica Division of Pfizer Hospital Products Group, Inc. (New York, N.Y.). The P.C.A. ® system includes, in addition to prosthetic femoral and tibial components, a prosthetic patellar component adapted for fixation to the natural patella, which component contacts the anterior plate portion of the femoral component when the knee joint is fully extended and cooperates with the femoral component during flexion of the prosthetic joint.

Despite the success of existing products such as the P.C.A. ® Total Knee System, differentiated prosthetic component designs are continuously sought which would more closely approach in use the anatomical function of the natural knee joint. One aspect of this anatomical function is the maximum achievable range of motion in joint flexion, which is about 150 degrees from full extension to full flexion in the natural human knee. Typically, a range of motion in flexion of only about 110 to 120 degrees is obtained with the use of known total knee prosthetic systems. Roughly half of this gap between the natural and prosthetic ranges of motion can be attributed to the inherent clinical and surgical situation, for example scarring within the knee joint, posterior ligament laxity and loss of the superpatellar pouch. However, the remainder of the gap can, in principle, be closed by appropriate modifications of prosthetic component geometries. Of particular concern is the effect of component geometries on the quadriceps muscle which extends from the femur over the patella (kneecap) to the tibia.

The quadriceps muscle experiences significant tension whenever the knee is not fully extended. This muscle controls extension of the knee (by contracting) but resists flexion. Typically, when conventional prosthetic knee components are used the quadriceps tension at flexion angles above about 90 degrees (from full extension) is substantially greater than in the natural anatomic human knee. Additionally, with the use of some prosthetic systems the quadriceps tension continues increasing with increasing flexion beyond an about 90 degree flexion angle, while in the natural human knee the quadriceps tension remains approximately constant in this high range of flexion. As a result of the excessive (and in some cases continuously increasing) quadriceps muscle tension resisting flexion, the maximum flexion angle that can be realized with the prosthetic knee joint is significantly limited.

SUMMARY OF THE INVENTION

It is an object of the present invention to provide a knee joint prosthesis in which the components of the prosthesis are configured and dimensioned such that the quadriceps muscle tension approximates that in the natural human joint throughout the full range of flexion of the prosthetic joint, in particular at flexion angles above about 90 degrees from full extension, so that the maximum range of motion of the prosthetic joint in flexion is increased.

This and other objects of the invention are achieved with a novel knee joint prosthesis including a tibial component adapted to be secured to the proximal tibia and having a spaced pair of condylar bearing portions; a patellar component adapted to be secured to the patella and having a patellar bearing surface; and a femoral component adapted to be secured to the distal femur and having an anterior plate portion adapted to contact said patellar bearing surface with the prosthetic knee joint at full extension, spaced lateral and medial condylar bearing portions adapted for mutual articulation with said tibial condylar bearing portions, and a web portion joining said two femoral condylar bearing portions at their anterior ends and along at least a part of their respective lengths from said anterior ends, said femoral condylar bearing portions having generally convex bearing surfaces and said web portion having a concave bearing surface, said anterior plate portion, femoral condylar bearing surfaces and web portion bearing surface defining together a continuous track to cooperate with said patellar bearing surface and guide the patellar component during flexion of the prosthetic knee joint from a fully extended state to a fully flexed state, and with the bearing surface of said lateral femoral condylar bearing portion, as viewed in transverse cross sections through said femoral bearing portion along said track, being steeply sloped towards said web portion over at least the innermost one-third of the width of the bearing portion so as to substantially deepen the lateral wall of said track guiding the patellar component and thereby reduce the tension on the quadriceps mechanism at high degrees of flexion and substantially increase the maximum level of flexion achievable with the prosthetic knee joint. In a preferred embodiment, the bearing surface of the lateral femoral condylar bearing portion exhibits, as viewed in transverse cross sections through said bearing portion along said track, a smooth continuous line consisting essentially of, from outside to inside, a first arcuate segment having a radius of curvature $R_1$, a second segment, and a third arcuate segment having a radius of curvature $R_2$, said second segment being relatively flat, $R_2$ being at least about 2.5 times $R_1$, and the arc length of the third segment being at least about as long as the length of said second segment.

The preferred embodiment of the bearing surface of the patellar component, which bearing surface cooperates in use with the femoral component, includes a dome, having substantially the shape of a part of a sphere, surrounded on all sides by a relatively flat peripheral portion. The peripheral portion is not symmetric about the dome but is instead extended in span, and tapered in width, along one direction substantially corresponding to the horizontal/lateral direction in use. Thus in this preferred embodiment the bearing surface presents a generally shield-shaped overall profile to the femoral component. It is also preferred that the patellar bearing surface be generally complementary with the surface of the femoral component track receiving it and that the femoral component web portion be extended sufficiently that it contacts the patellar component bearing surface throughout said high degrees of flexion up to said maximum level of flexion, so that the patellar component is fully supported and stabilized by the femoral component at said high degrees of flexion.

The present invention also comprises a novel adjustable sizing gauge in combination with a femoral drill jig employed in the surgical implantation of the knee joint prosthesis of the invention.

DETAILED DESCRIPTION OF THE INVENTION

The various aspects of the present invention will be described in detail with reference to certain preferred embodiments thereof. Reference to these embodiments does not limit the scope of the invention, which is limited only by the scope of the claims.

In the drawings:

FIG. 1 is an exploded perspective view of a right knee joint prosthesis of the invention, showing femoral, tibial and patellar components;

FIG. 2 is a sectional view taken along line 2—2 in FIG. 1;

FIGS. 3, 4 and 5 are top, front and rear plan views, respectively, of the femoral component shown in FIG. 1;

FIG. 6 is a sectional view corresponding to FIG. 2, but showing the femoral, tibial and patellar components cooperatively engaged with the prosthetic joint at full extension;

FIG. 7 is a sectional view corresponding to FIG. 6, but with the prosthetic joint at full flexion;

FIGS. 11 and 12 are side and bottom plan views, respectively, of an adjustable sizing gauge/femoral drill jig combination of the invention; and FIG. 13 is a sectional view taken along line 13—13 in FIG. 10.

Figure 8:
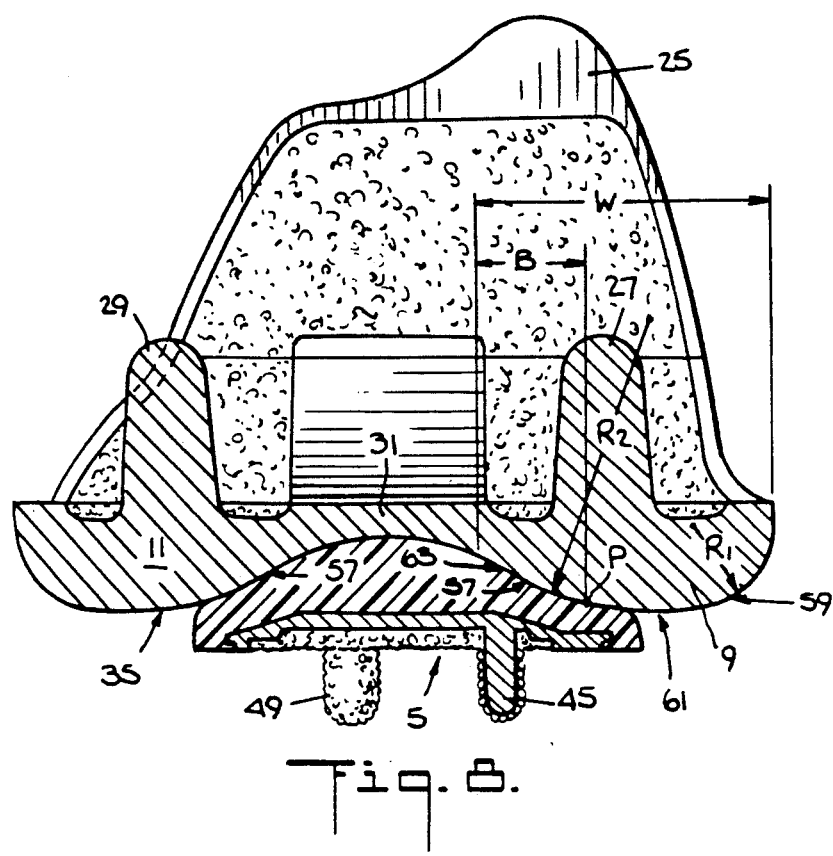
FIG. 8 is a sectional view taken along line 8—8 in FIG. 7.

A knee joint prosthesis 1 of the present invention is shown in FIGS. 1 and 2. This prosthesis includes a tibial component 3 adapted to be secured to the proximal tibia, a patellar component 5 adapted to be secured to the patella and a femoral component 7 adapted for securement to the distal femur. Component 7 includes spaced apart lateral and medial condylar bearing portions 9 and 11, respectively, which are adapted for mutual articulation with a spaced pair of condylar bearing portions 13 and 15 of the tibial component 3. The particular configuration of component 3 is not critical to the present invention. In the embodiment shown in the figures, component 3 includes a plastic (e.g. ultra-high molecular weight polyethylene) insert 17 (which in turn includes the bearing portions 13 and 15) held by and secured by known means to a metallic tray 19. The tibial tray 19 includes a stem 21 having a cruciform cross-sectional shape and a base 23 supporting the insert 17. A porous coating (for example of the kind disclosed in U.S. Pat. No. 4,550,448) may be provided on some or all of the lower surface of the base 23 to enhance the fixation of component 3 to the resectioned proximal tibia by cementation or tissue ingrowth.

The femoral component 7 is a unitary, one-piece article preferably made of a suitable metal or metal alloy such as a cobalt-chromium-molybdenum alloy, titanium or a titanium alloy. In addition to its spaced bearing portions 9 and 11, component 7 includes an anterior plate portion 25 (the anterior anatomic reference direction is to the right in FIGS. 2 and 6 and the posterior direction to the left) having an anterior surface 26, a pair of fixation pegs 27 and 29 adapted for placement within pre-drilled holes in the resectioned distal femur, and a web portion 31 joining bearing portions 9 and 11 at their anterior ends (adjacent plate portion 25) and along the respective lengths of bearing portions 9 and 11 until the vicinity of the fixation pegs 27 and 29. The medial bearing portion 11 is curved in a top plan view of component 7 (see FIG. 3), while the lateral bearing portion 9 is essentially straight. A porous coating (see, e.g., U.S. Pat. No. 4,550,448) may be provided on some or all of the inner surfaces of portions 9, 11 and 25 to enhance the fixation of component 7 to the resectioned distal femur by cementation or tissue ingrowth. Additionally, if desired, such a coating may be provided on the pegs 27 and 29. The lateral femoral condylar bearing portion 9 has a generally convex bearing surface 33, the medial femoral condylar bearing portion 11 has a generally convex bearing surface 35, and the femoral web portion 31 has a concave bearing surface 37.

The patellar component 5 includes a plastic (e.g. ultra-high molecular weight polyethylene) bearing portion 39 secured by known means to a metallic fixation insert 41, which may be made for example of the same metal or metal alloy as the femoral component 7. Insert 41 comprises a base 43 and a plurality (three, for example) of fixation pegs 45, 47 and 49 adapted for placement within pre-drilled holes in the patella. A porous coating (see, e.g., U.S. Pat. No. 4,550,448) may be provided on the pegs 45, 47 and 49 and on some or all of the anterior surface of insert 41 to enhance the fixation of component 5 to the resected patella by cementation or tissue ingrowth.

Figure 9:
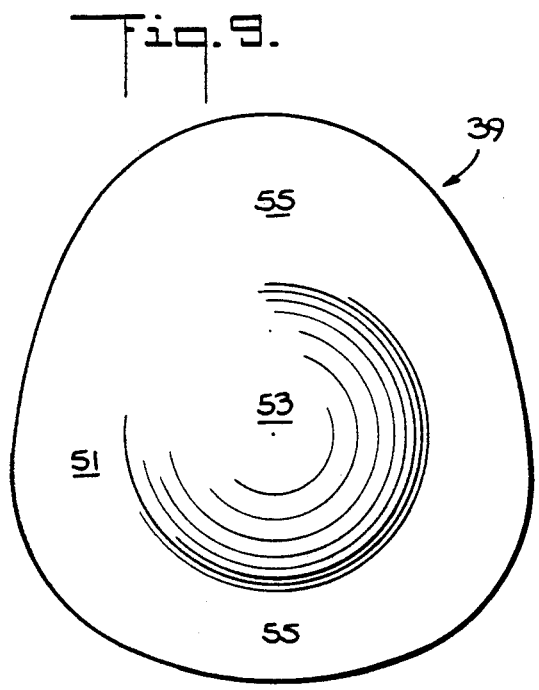
FIGS. 9 and 10 are rear and front plan views, respectively, of the patellar component shown in FIG. 1.
Figure 10:
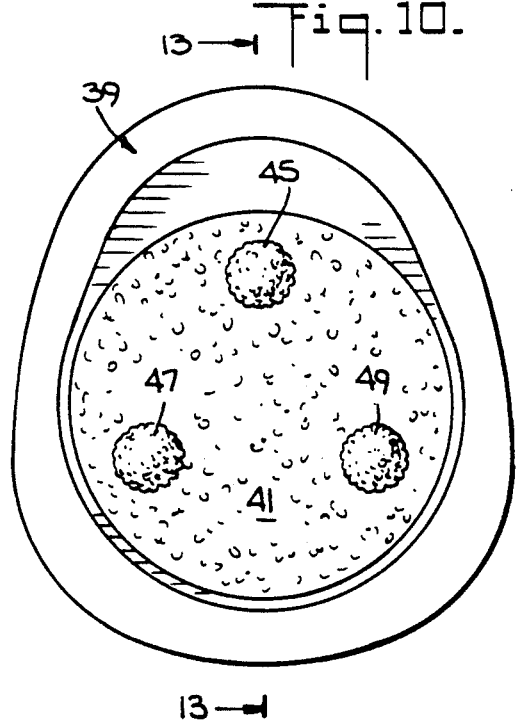

The bearing portion 39 defines the posterior surface of the patellar component 5, i.e., the patellar bearing surface 51 facing the femoral component in use. In the embodiment of the invention illustrated in the figures, the bearing surface 51 comprises a dome 53, having the shape of a part of a sphere, surrounded around its full circumference by a relatively flat peripheral portion 55. Preferably, as shown in the figures, peripheral portion 55 is asymmetric with respect to dome 53 and is extended in length (i.e. span) along one direction. In use, the patellar component 5 is implanted so that this direction substantially corresponds to the horizontal/lateral direction (see FIG. 1). More preferably, as also shown in the figures, the peripheral portion 55 is slightly concave with a substantially constant radius of curvature throughout. Thus, the patellar bearing surface 51 presents a generally shield-shaped overall profile to the femoral component (see FIG. 9), with the thinner end of the shield pointing away from the center line of the patient's body.

In use, the patellar bearing surface 51 contacts the anterior plate portion 25 of the femoral component 7 when the prosthetic knee joint is at full extension (see FIG. 6). In that state the patellar component 5 is adjacent the beginning of a continuous patellar component-guiding track 57 defined together by surfaces 26, 33, 35 and 37 of portions 25, 9, 11 and 31, respectively, of the component 7. (This track is angulated by about 3 to 4 degrees upwardly/laterally in the plate portion 25 and the adjacent parts of portions 9, 11 and 31, as is shown in FIG. 4). Preferably, the patellar bearing surface 51 is generally complementary with the surface of track 57. As the prosthetic knee joint is flexed from a fully extended state (see FIG. 6) to a fully flexed state (see FIG. 7), the track 57 cooperates with the patellar bearing surface 51 and guides the patellar component 5 riding in the track. As is shown in the figures the femoral web portion 31 ends in the vicinity of the femoral fixation pegs 27 and 29. Also, the center of the patellar bearing surface dome 53 will reside in the same vicinity when the prosthetic knee joint is fully flexed (typically to about 130 to about 140 degrees from full extension). Thus, the femoral web portion 31 fully supports the patellar component 5 throughout the entire range of moderate and high joint flexion. The full support of patellar component 5 by femoral component 7 over an extensive contact area protects the resected patella, the patellar component 5 and the interface between the patella and component 5 against the relatively high bending forces developed beyond 90 degrees of flexion (from full extension). This improves the stability of the knee joint prosthesis 1 by reducing the risk of failure by fracture of the patella, separation of patellar component bearing portion 39 from insert 41, or loosening of the patellar bone-patellar component interface. However, it is contemplated that web portion 31 could be extended posteriorly beyond, or alternatively terminated short of, the vicinity of pegs 27 and 29. In the latter case the femoral condylar bearing surfaces 33 and 35 would alone define the portion of the track 57 travelled by the patellar component 5 at the highest levels of flexion.

Of substantial importance to the present invention is the cross-sectional shape of the femoral condylar bearing surfaces 33 and 35 in those regions of bearing portions 9 and 11 intended to contact the patellar bearing portion 39 in use. As is best shown in FIG. 8, along the track 57 the bearing surface 33 of the lateral femoral condylar bearing portion 9 is steeply sloped inwardly (i.e. to the left in FIG. 8 towards the web portion 31 and the femoral intercondylar notch) over more than the innermost one-third of the width W of the lateral bearing portion 9, as viewed in the transverse cross-sectional view of FIG. 8 through bearing portion 9. As a consequence of this steep inclination of bearing surface 33, the lateral wall of the track 57 is substantially deepened and the patellar compnent 5 is able to ride deeply upon (i.e. sink deeply into) the femoral component 7 as the prosthetic knee joint is being flexed. This in turn significantly reduces the tension on the quadriceps mechanism (which is stretched over the patella and patellar component 5) at high degrees of flexion and substantially increases the maximum range of motion in flexion achievable with the prosthetic knee joint, up to typically about 130 to about 140 degrees from full extension. Note that the boundary between bearing portion 9 and web portion 31 in FIG. 8 is at the point of inflection on the surface of the track 57.

In the preferred embodiment shown in the figures, the lateral femoral condylar bearing surface 33 exhibits, as viewed in transverse cross sections through bearing portion 9 along track 57 (see FIG. 8) a smooth continuous line consisting essentially of a first arcuate outer segment 59, which runs into a second relatively flat middle segment 61, which runs in turn into a third arcuate inner segment 63. In this preferred embodiment the radius of curvature $R_2$ of segment 63 is at least about 2.5 times the radius of curvature $R_1$ of segment 59, the arc length of segment 63 is at least about as long as the length of segment 61, and segment 63 begins at a point P which is at a distance B from the inner extremity of the bearing portion 9 in the transverse cross section, with B being at least one-third of W.

The deep tracking of the patellar component 5 can be further enhanced if both of the femoral condylar bearing surfaces 33 and 35, as viewed in transverse cross sections through the bearing portions 9 and 11, are steeply sloped inwardly over at least the innermost one-third of the width of the bearing portion. Thus, for example, both of the bearing surfaces 33 and 35 can be designed to satisfy the detailed parameters set forth for bearing surface 33 in the preceding paragraph above.

The components of the knee joint prosthesis 1 of the present invention may be implanted in a patient in substantially the same manner as with the known technique for implanting the components of the aforementioned P.C.A. ® Total Knee System (see the publically available publication, "The P.C.A ® Primary Total Knee System Surgical Technique", copyright 1984 by Pfizer Hospital Products Group, Inc.). Reference is also made to the related U.S. Pat. No. 4,646,729. This publication and this patent are both incorporated by reference herein in their entireties. In addition, a novel piece of instrumentation useful in the implantation of a knee joint prosthesis of the present invention and other knee joint prostheses as well (such as the known P.C.A. ® System) is shown in FIGS. 11 and 12. This novel piece of instrumentation 101 comprises a femoral drill jig 103 in combination with a femoral component sizing gauge 121.

The femoral drill jig 103 is similar to the one disclosed in the aforementioned U.S. Pat. No. 4,646,729. Jig 103 comprises a base 105 having a flat inner surface 106, a pair of skids 107 and 109 extending from base 105 at its lower end, a pair of drill holes 111 and 113 through base 105 for forming femoral component fixation holes, a pair of handles 137 and 139 and a pair of retractable fixation pins 133 and 135 for temporarily affixing jig 103 to the patient's femur.

The sizing gauge 121 comprises a body portion 122 and an elongated stylus 123 slidably received within a bore 127 in portion 122. Preferably stylus 123 and bore 127 are designed so that relative rotation about the axis of bore 127 is not permitted. Stylus 123 includes an indicating tip 125 and a handle 141, and is further provided with a series of reference marks 143 corresponding to different femoral component sizes (for example, small, medium and large). The sizing gauge 121 is rotatably and releasably attached to the drill jig 103 by the insertion of cylindrical body portion extension 129 into closed cylindrical bore 131 in the base 105.

The combination 101 is used in the implantation procedure after the flat distal cut has been made through the femoral condyles, but before the anterior and posterior cuts have been made. With fixation pins 133 and 135 retracted, and sizing gauge 121 not yet attached, the two skids 107 and 109 are placed between the resected posterior femoral condyles and the tibial plateaus. The drill jig is then properly centered in the medial/lateral aspect and then temporarily affixed to the femur by impacting the fixation pins 133 and 135. At this point the inner face 106 should be flush against the cut femoral surface.

The sizing gauge 121 is then attached to the drill jig 103. The gauge 121 is used as a reference for femoral component selection. The tip 125 of the stylus 123 is placed on the most prominent aspect of the anterior cortex of the femur, which is usually slightly to the lateral side. In this manner, the tip 125 indicates the intersection of the anterior femoral cut and the cortex of the femur. The estimated proper femoral component size and the appropriate anterior-posterior femoral cutting jig are determined by reading the point at which the face 145 of body portion 122 intersects the series of lines 143. Two holes are drilled through holes 111 and 113 to receive two positioning studs of the anterior-posterior femoral cutting jig. Later in the implantation procedure these two holes may be widened to receive femoral component fixation pegs (e.g. pegs 27 and 29 of component 7).

I claim:

1. In combination:

a femoral drill jig comprising a base having a flat inner surface, an upper end and a lower end, a pair of skids extending inwardly from said base at the lower end thereof for placement between the resected posterior femoral condyles and tibial plateaus, and a plurality of drill holes extending through said base for forming femoral component fixation holes; and a sizing gauge for indicating an appropriate femoral component size comprising a body portion and an elongated stylus slidably received within a bore in said body portion, said stylus being provided with a series of indicia along its length corresponding to different femoral component sizes and having an indicating tip for indicating a point on the surface of the anterior femoral cortex, said femoral drill jig and said sizing gauge respectively including cooperating means for attachment of said body portion to said base adjacent the upper end of said base, said attachment means permitting rotation of said body portion with respect to said base about an axis substantially parallel to said inner surface.

* * * * *